United States Patent [19]
Grahn

[11] Patent Number: 5,683,438
[45] Date of Patent: Nov. 4, 1997

[54] APPARATUS AND METHOD FOR CORE BODY WARMING OF MAMMALS EXPERIENCING HYPOTHERMIA

[75] Inventor: Dennis A. Grahn, Palo Alto, Calif.

[73] Assignee: Stanford University, Stanford, Calif.

[21] Appl. No.: 402,469

[22] Filed: Mar. 10, 1995

[51] Int. Cl.[6] ........................................ A61F 7/00
[52] U.S. Cl. .................... 607/104; 607/114; 607/88; 607/96; 607/100; 126/204
[58] Field of Search ................ 607/88–96, 100, 607/104, 107–112, 114; 165/46; 383/90; 126/204; 601/15

[56] References Cited

U.S. PATENT DOCUMENTS

| | | | |
|---|---|---|---|
| 4,648,392 | 3/1987 | Cartier et al. | 607/104 |
| 5,074,285 | 12/1991 | Wright | 607/111 |
| 5,149,331 | 9/1992 | Ferdman et al. | 607/96 |
| 5,241,958 | 9/1993 | Noeldner | 607/104 |
| 5,441,477 | 8/1995 | Hargest | 607/104 |

Primary Examiner—Angela D. Sykes
Assistant Examiner—Robert L. Nasses, Jr.
Attorney, Agent, or Firm—Lumen Intellectual Property Services

[57] ABSTRACT

The invention presents an apparatus and a method for core body warming of hypothermic mammals. The apparatus has an enclosing element to be placed around a predetermined body portion of a mammal in a vacuum-tight manner and a vacuum system connected to the enclosing element for generating and maintaining a predetermined negative pressure, preferably between −20 mmHg and −80 mmHg, inside the enclosing element. A heating unit delivers a thermal energy while the vacuum system is maintaining the predetermined negative pressure. The simultaneous application of thermal energy and negative pressure produces vasodilation which promotes absorption of the thermal energy through the surface of the body portion. The circulatory system of the mammal naturally carries the thermal energy to the core body of the mammal.

20 Claims, 3 Drawing Sheets

APPARATUS AND METHOD FOR CORE BODY WARMING OF MAMMALS EXPERIENCING HYPOTHERMIA

BACKGROUND

1. Field of the Invention

The present invention relates to the field of thermal therapeutic applications, and in particular to core body warming in the treatment of hypothermia.

2. Description of Prior Art

Hypothermia results from exposure to conditions where the body cannot generate sufficient heat to compensate for the body heat lost to the environment. Hypothermia impedes normal bodily functions and, if not reversed, can lead to death. Shivering and peripheral vasoconstriction are the body's primary physiologic mechanisms for generating and conserving heat, respectively.

Hypothermia occurs in conditions where the body is exposed to ambient temperatures well below normal physiologic temperature such as immersion in cold water. Hypothermia also results from the administration of general anesthesia. Under general anesthesia, mammals lose the ability to conserve heat by constriction of peripheral blood vessels ("vasoconstriction") or generate heat by shivering ("thermogenesis") in response to cold challenges. As a result, many individuals emerging from general anesthesia experience hypothermia, particularly if the time under general anesthesia is prolonged.

In general, active core rewarming of the body is desired following general anesthesia or other prolonged physiologic exposure to cold. Peritoneal dialysis using warming fluids can be used in cases of severe hypothermia, but this method is invasive and exposes the less severely hypothermic patient to unwarranted risks of morbidity and mortality. Less severe hypothermia can be treated pharmacologically with muscle relaxants, but this intervention decreases shivering which, in turn, impedes physiologic warming and increases the time required to restore normal body temperature. Radiant heat, warm water, or warm air applied to the skin surface alone has only a minimal effect on raising core body temperature because peripheral vasoconstriction impedes heat transfer from the skin to the body core. Breathing warm, humidified air provides some deep body core heating, and there are devices commercially available for that purpose. Inhalation warming methods, however, are relatively slow-acting and may require invasive techniques such as tracheal intubation for effective use.

The challenge has been to develop a means to rapidly, safely, and effectively bring the core body temperature to within normal physiologic range following general anesthesia or other prolonged exposures to cold.

A variety of devices and techniques are known for the therapeutic heating of a part of the body, but these generally are neither designed nor adequate for the transmission of heat to the core of the body. U.S. Pat. No. 4,736,088 describes an electrically driven heating pad and muff structure which directs the flow of heat through a laminate to produce moist heat on a body member.

U.S. Pat. No. 4,747,409 describes a sleeve that contains electric resistance heating elements designed to fit over a body extremity for the purpose of dilating blood vessels; and U.S. Pat. No. 5,074,285 is a device that encloses a human extremity and applies static heat to that extremity simultaneously with a gradient pressure applied repeatedly in timed sequence from a distal to proximal portion of an extremity. Both of these devices will be ineffective for the treatment of hypothermia because heat applied to the surface of the skin in this manner will not allow the heat to penetrate into the body core.

Another prior-art device for core body warming uses radio frequency waves. U.S. Pat. No. 4,685,462 describes an apparatus that employs mutually inductive first and second helical coils positioned around the torso of a body to produce radio frequency waves that directly rewarm the core body. This device does not have the flexibility to fit around an appendage and may interfere with surgical intervention of the chest and abdomen. In addition, this device may cause disruptive electromagnetic interference in the operating theater or recovery room following general anesthesia.

OBJECTS AND ADVANTAGES OF THE INVENTION

With the foregoing in mind, it is a principal object of this invention to provide a safe, non-invasive apparatus and method for effectively rewarming the core body of patients who have undergone general anesthesia or otherwise have developed hypothermia.

It is another object of this invention to provide a practical core body warming device which will provide heating substantially throughout a central body region containing the heart, can be used safely both in a hospital environment and, in its most portable form, can be easily attached to a hypothermic victim and be safely used as first-aid in a rescue operation.

It is another object of this invention to provide a core body heating apparatus wherein the apparatus is automatically adaptable to subjects of different size and mass.

These and other objects and advantages will become more apparent after consideration of the ensuing description and the accompanying drawings.

SUMMARY OF THE INVENTION

It has been found that by placing a body part such as an arm or a leg in a negative pressure environment, it is possible to vasodilate the capillary beds in that body part. Once the capillary beds have been vasodilated, thermal energy supplied to the skin of that body part is efficiently transduced directly to the core body. Since the remainder of the peripheral vasculature remains vasoconstricted, the distribution of the heat applied to the vasodilated skin regions will be confined to the core body.

In particular, the invention presents a core body warming apparatus having an enclosing element, preferably a pliant sleeve or tube, which is placed around a predetermined body portion of a mammal. Seals establish a vacuum-tight fit between the sleeve and the body portion. The apparatus further includes a vacuum system connected to the sleeve for generating and maintaining a predetermined negative pressure, preferably between −20 mmHg and −80 mmHg, inside the sleeve. A heating unit, preferably a heating blanket or a set of chemical heating elements, is placed inside the sleeve for delivering a thermal energy to the surface of the body portion. A radiant heat source placed outside the sleeve can also be used to deliver the thermal energy. Simultaneously with the delivery of thermal energy the vacuum system maintains the predetermined negative pressure. This produces the local vasodilation which promotes absorption of the thermal energy through the surface of the body portion. The circulatory system of the mammal naturally carries the thermal energy to the core body of the mammal.

The invention further discloses a method for core body warming of mammals experiencing hypothermia. The method calls for application of the negative pressure ranging between −20 mmHg and −80 mmHg and simultaneous delivery of thermal energy to the body surface or skin. Furthermore, the predetermined negative pressure is oscillated for promoting the transport of the thermal energy to the core body of the mammal by its own circulatory system. The particulars relating to both the present apparatus and method are explained in detail in the following description and drawings.

BRIEF DESCRIPTION OF THE DRAWINGS

The presently preferred embodiments of the invention are illustrated in the accompanying drawing in which.

DESCRIPTION

Figure 1:
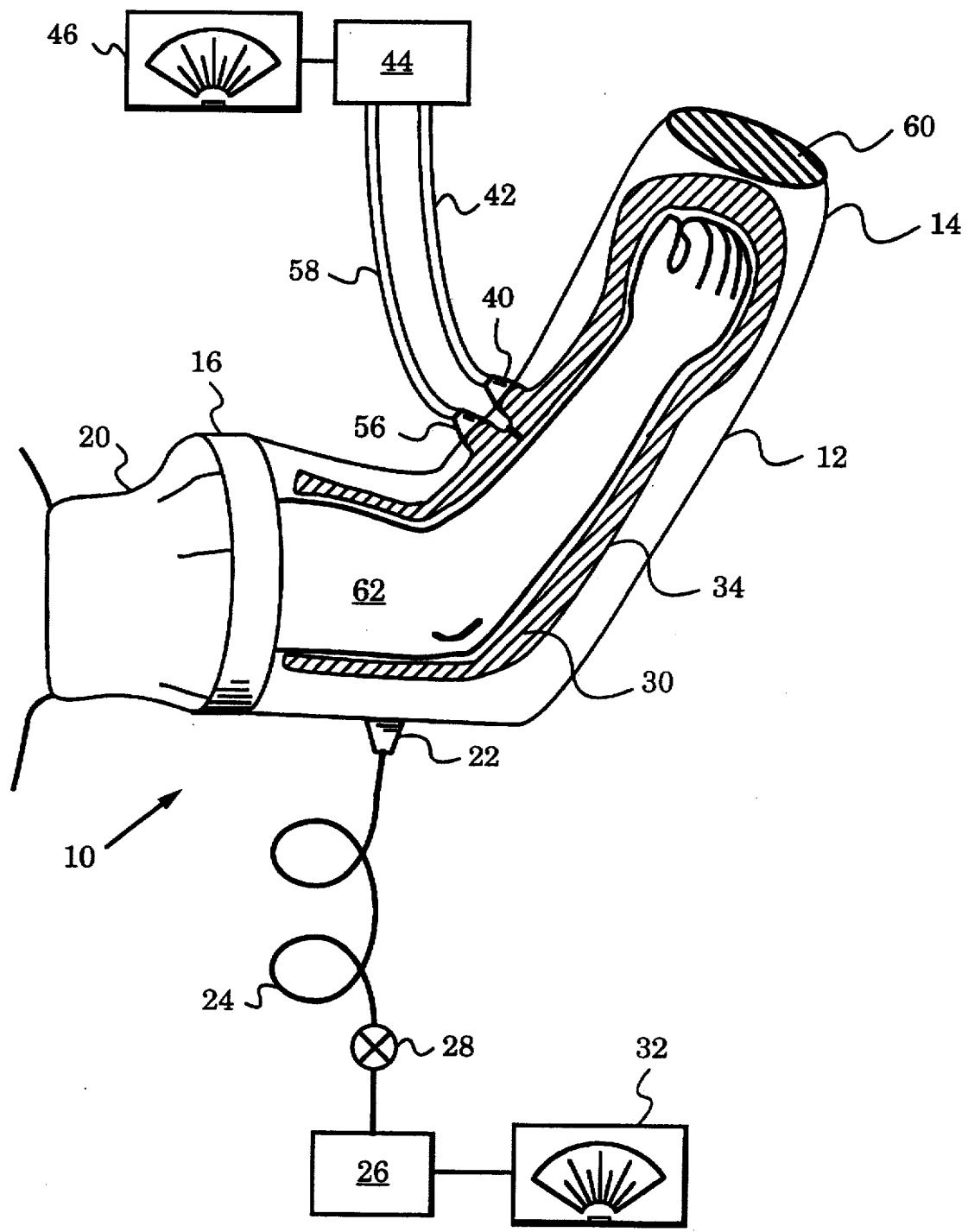
FIG. 1 is a perspective view of an enclosing structure according to the invention.

As shown in FIG. 1, a preferred embodiment of the present invention is a core body warming apparatus 10 with an enclosing element 12 in the form of a hollow, tubular, elongated sleeve. Sleeve 12 is dimensioned to fit around a body portion 62, preferably an appendage, as described below. In the embodiment illustrated in FIG. 1 appendage 62 is an arm.

Sleeve 12 can be made of virtually any non-hazardous material which retains the requisite shape while the interior of sleeve 12 is maintained at negative pressures. In particular, sleeve 12 has to support negative pressures down to at least −85 mmHg. In a preferred embodiment sleeve 12 is made of pliant and elastic materials which can include supporting or reinforcing members. This type of construction easily accommodates movements of arm 62 and thus provides a hypothermic patient more comfort and freedom. In the present embodiment sleeve 12 is a neoprene-impregnated polyester sheath supported on a spring steel wire helix.

Sleeve 12, as shown in FIG. 1, has a distal end or rim 14 and a proximal end or rim 16. Distal rim 14 is capped by a sealing element 60 capable of creating an airtight seal. In this embodiment element 60 is a plastic plate. However, a cap or other sealing element can be used with equal success. In fact, sleeve 12 may be closed off at distal end 14.

A flexible flange 20 is attached to proximal rim 16. Flange 20 is preferably made of a synthetic material impermeable to air. The tubular form of flange 20 ensures that it fits snugly around arm 62 and conforms to the arm's shape. In the present embodiment 20 is made of Neoprene (R).

Elongated sleeve 12 is provided with a pressure inlet 22. A pressure conduit 24, e.g., a flexible tube, is connected to inlet 22. The other end of conduit 24 is connected to a vacuum pump 26. Vacuum pump 26 is a standard pump capable of generating negative pressures down to −85 mmHg and beyond inside sleeve 12. The delivery of this negative pressure through conduit 24 can be regulated by any conventional mechanisms. In the embodiment shown, an adjustable valve 28 guarantees maintenance of the desired pressure inside sleeve 12. Conveniently, a readout gauge 32 is also provided for visual pressure indication.

A heating element 34 is lodged inside elongated sleeve 12. In the preferred embodiment, heating element 34 is a heating blanket filled with a heating fluid 30. Because of its high heat capacity and general safety, water is particularly well-suited for heating fluid 30. Heating blanket 34 extends along the length of sleeve 12 and wraps around arm 62. In fact, it is desirable that the area of contact between arm 62 and blanket 34 be as large as possible.

Blanket 34 is connected to a fluid inlet 40 and a fluid outlet 56. A supply conduit 42 and a return conduit 58, both preferably made of a flexible tubing, are attached at inlet 40 and outlet 56 respectively. At their other ends conduits 42 and 58 are connected to a heating and circulating system 44. Preferably, system 44 is a fluid heater and a circulating pump (not shown). Suitable heaters and pumps are commercially available and commonly known. In addition, system 44 has a control indicator 46 for indicating the temperature of fluid 30 and its rate of flow.

Core body warming apparatus 10 is simple to use. First, a hypothermic person's arm 62 is placed inside sleeve 12 such that heating blanket 34 envelops arm 62 and remains in contact with it. In this position, flange 20 wraps around the upper portion of arm 62. To ensure that flange 20 conforms closely to the contour of the upper portion of arm 62 the latter is preferably bare.

With arm 62 properly inserted into sleeve 12, pump 26 is activated to produce a negative pressure between −20 mmHg and −85 mmHg inside sleeve 12. Under the influence of negative pressure or suction, flange 20 seals tightly around the upper part of arm 62 to preserve the vacuum inside sleeve 12. At the same time, heating and circulating system 44 is also activated to warm up and pump heating fluid 30 through heating blanket 34. In particular, heated fluid 30 is delivered through supply conduit 42 and recirculated through return conduit 58. Control indicator 46 is used for setting the proper flow rate and temperature of fluid 30. In a preferred embodiment, the amount of thermal energy delivered to the surface of arm 62 is determined based on the body weight of the patient and his initial body temperature.

In particular, the thermal energy required for initial heat-up is determined by the following equation:

$$E_{req} = \frac{\text{heat absorption} + \text{heat loss} - \text{metabolic heat production}}{\text{time}} \quad [1]$$

Since metabolic heat production in anesthetized subjects is negligible, equation [1] can be simplified to state:

$$E_{req} = \frac{\text{heat absorption} + \text{heat loss}}{\text{time}} \quad [2]$$

Heat absorption is calculated from the below equation:

$$\text{Heat absorption} = \frac{\text{specific heat} \cdot \text{body weight} \cdot \Delta T}{3412 \text{ (Btu/kwh)}}, \quad [3]$$

where specific heat is expressed in British thermal units (Btu) and the body weight in pounds. $\Delta T$ stands for the temperature difference between the initial and the final or desired body temperature. Heat loss is computed according to the equation:

$$\text{Heat loss} = \text{specific heat loss} \cdot \text{exposed surface area} \cdot \text{time}. \quad [4]$$

Rewriting equation [3] under the assumption that the specific heat of a human being is 0.92 Btu/lb·°F. and substituting equation [4] one obtains:

$$\text{Heat absorption} = 0.00027 \text{ (kwh/lb·°F.)} \cdot \text{weight} \cdot \Delta T. \quad [5]$$

This means that every 100 pounds of body weight must absorb 0.027 kw of heat per hour to warm up by one degree Fahrenheit. In practice, some variations in this value will be found between human beings and other mammals.

The heat lost by a patient will depend on the size of the exposed area. Frequently, only the face is uncovered. This offers a surface area of approximately 1 sq.ft. to the escaping heat. Under these conditions, the heat loss is approximately 75 watts per hour. Typically, recovery from anesthesia takes 45 minutes, meaning that it is most desirable to rewarm during the same amount of time. Substituting this data in equation [2] and calculating the thermal energy required for warming up each 100 pounds of body weight, one obtains 316 Watts. This is the actual power needed to rewarm the core body in 45 minutes.

The thermal energy which can be safely delivered to the skin by blanket 34 greatly exceeds the 316 Watts computed above. For example, the preferred embodiment uses water at 43° C. as heating fluid 30 moving at a flow rate of 5 l/min. This enables deliveries of thermal energies greatly exceeding the 316 Watts required to warm up the core body and sufficient to overcome typical system losses.

There are two simultaneous effects on arm 62. The negative pressure inside sleeve 12 causes local vasodilation of the capillary beds while heating fluid 30 supplies thermal energy to the skin. Vasodilated capillaries are very efficient at absorbing heat. They take up the thermal energy offered by blanket 34 and carry it to the core body. Since the remainder of the peripheral vasculature remains vasoconstricted, the distribution of the heat applied to the vasodilated skin regions will be confined to the body core.

To further aid the body in absorbing the thermal energy delivered, the negative pressure value can be changed. For example, a periodic fluctuation or oscillation between −20 mmHg and −85 mmHg may be introduced. The period can be in rhythm with the patient's heart rate. This oscillation will maximize the heat transfer to the core body.

The above apparatus and method of use are safe, non-invasive, and very efficient in rewarming the core body of patients who have undergone general anesthesia or otherwise have developed hypothermia.

Figure 2:
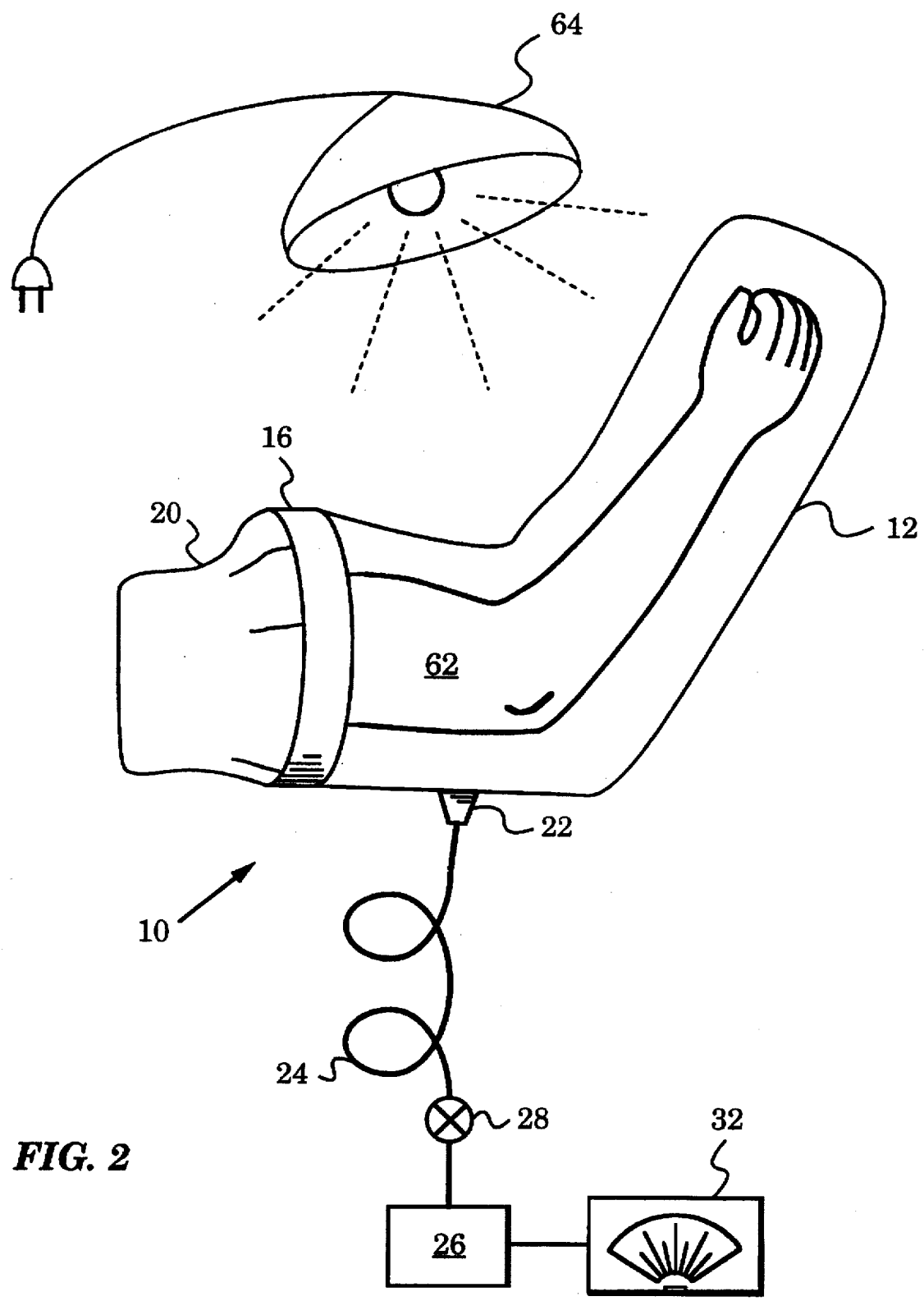
FIG. 2 is a perspective view of an alternative embodiment of the present invention.

An alternative embodiment of the apparatus of the invention is shown in FIG. 2. Elements shared in common with the preferred embodiment shown in FIG. 1 are labelled with the same reference numbers. In this embodiment the heating blanket and corresponding heating and circulating system are replaced by a radiant heat lamp 64 positioned above sleeve 12. The material of sleeve 12 is chosen to transmit the light generated by lamp 64 while satisfying all the requirements listed above. Preferably, lamp 64 emits infrared light.

The embodiment of FIG. 2 operates analogously to that of FIG. 1. After arm 62 is placed inside sleeve 12 vacuum pump 26 produces a negative pressure inside it and causes flange 20 to seal around arm 62. Simultaneously, lamp 64 is turned on to deliver radiant heat. The radiant heat passes through sleeve 12 and carries its thermal energy to the skin of arm 62. Since arm 62 is subjected to negative pressure its capillaries are dilated and thus easily absorb and transfer the thermal energy supplied to the skin. As above, that thermal energy is used by the patient's circulatory system to warm the body core.

Figure 3:
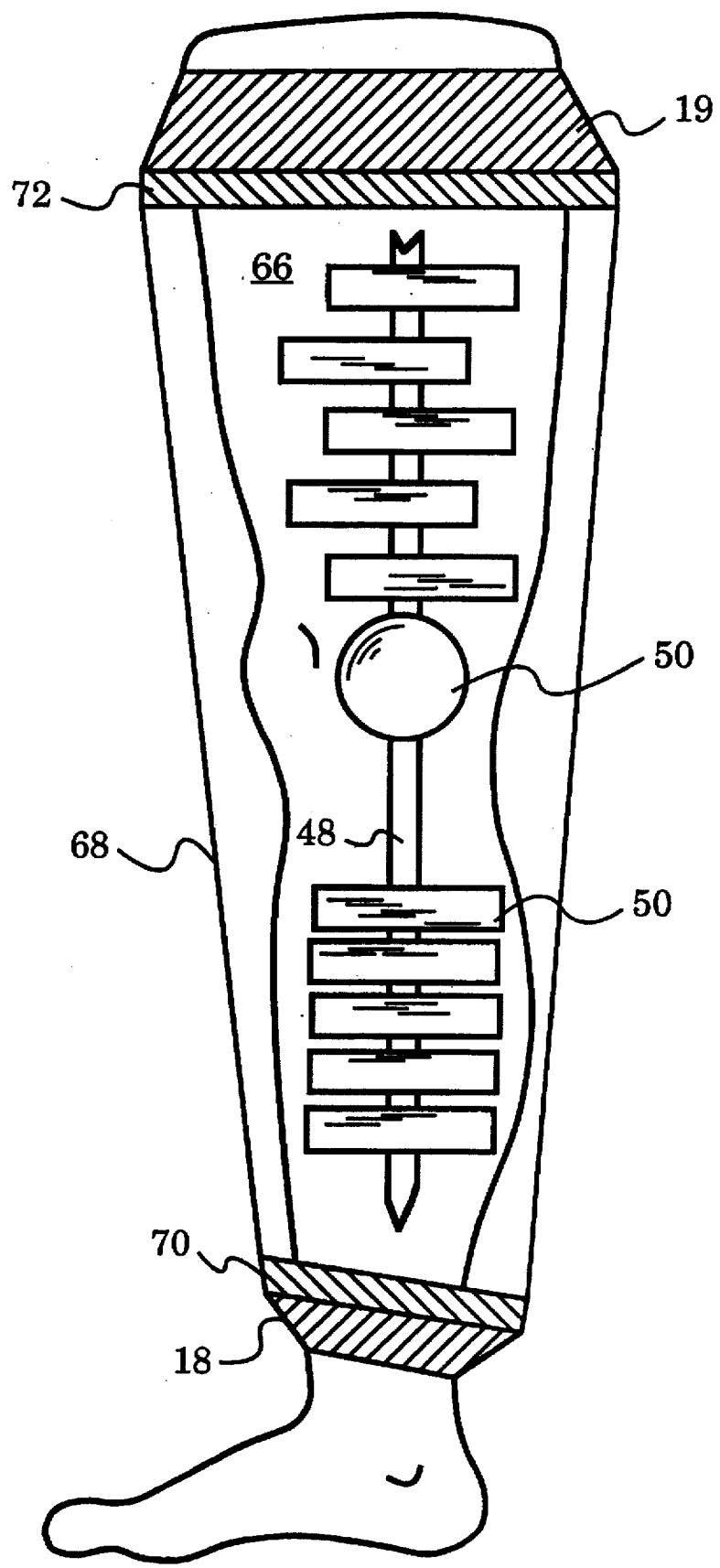
FIG. 3 is a perspective view of another embodiment of the present invention.

FIG. 3 illustrates an embodiment of the invention which is adapted for enclosing a leg 66. In particular, a sleeve 68 designed to be pulled over leg 66 has a bottom rim 70 and a top rim 72. Also, sleeve 68 is reinforced, e.g., by an internal helical spiral (not shown), against collapse under negative pressure. Two flanges 18 and 19 are attached to rims 70 and 72 respectively. Flanges 18 and 19 are analogous in all respects to flange 20 of the earlier embodiments.

A support rod 48 is located inside sleeve 68. A number of conventional chemical heating elements 50 are mounted on rod 48. The vacuum system connected to sleeve 68 is not shown in FIG. 3.

The embodiment of FIG. 3 operates analogously to the previous embodiments with the difference that thermal energy is delivered to the skin of leg 66 by chemical heating elements 50. This method of delivering heat is more practical outside hospitals and controlled environments, e.g., in the wilderness during a search-and-rescue operation.

All three of the above mentioned embodiments can be used for human patients and other mammals. The size and shape of the enclosing element or sleeve will differ according to the body part around which the apparatus is placed.

SUMMARY, RAMIFICATIONS, AND SCOPE

The above embodiments of the present invention are only illustrative in purpose and in no way limit the scope of the invention. Many alterations and improvements can be introduced to the above-described embodiments without going beyond the scope of the invention. It is possible to use the present invention to render a patient hypothermic by withdrawing heat from the patient while sustaining a vacuum. The vasodilation produced by the negative pressure will aid in efficiently dissipating heat and lowering the core body temperature.

Obviously, other embodiments and modifications of the invention will readily come to the mind of one skilled in the art having the benefit of the teachings presented in the foregoing description and drawings. Therefore, the scope of the invention should be determined, not by examples given, but by the appended claims and their legal equivalents.

I claim:

1. A system for treating a mammal experiencing hypothermia, said system comprising:

a) an enclosing means for enclosing a body portion of said mammal;

b) a sealing means mounted on said enclosing means for establishing a vacuum-tight fit between said body portion and said enclosing means;

c) a vacuum system connected to said enclosing means for generating and maintaining a predetermined negative pressure inside said enclosing means, thereby causing vasodilation in said body portion; and d) a heating means for delivering a thermal energy to the surface of said body portion while said vacuum system is maintaining said predetermined negative pressure, so that the local vasodilation in said body portion promotes absorption and transfer of said thermal energy from the surface of said body portion to the core body of said mammal.

2. The system of claim 1 wherein said heating means comprises a heating blanket with a heating fluid, said heating blanket is arranged circumferentially inside said enclosing means, and said heating blanket is adapted to maintain contact with at least a part of the surface of said body portion.

3. The system of claim 1 wherein said enclosing means comprises a generally tubular sleeve having a distal rim and a proximal rim, said sealing means comprises a lower seal mounted on said distal rim and an upper seal mounted on said proximal rim, said body portion comprises an extremity, and said sleeve has a diameter substantially larger than said extremity such that at least a part of said extremity fits inside said tubular sleeve.

4. The system of claim 3 wherein said tubular sleeve comprises a pliant material for accommodating movements of said extremity.

5. The system of claim 3 wherein said heating means comprises a heating blanket with a heating fluid, said heating blanket is arranged circumferentially inside said enclosing means, and said heating blanket is adapted to maintain contact with at least a part of said extremity.

6. The system of claim 5 wherein said upper seal comprises a flexible flange adapted to fit snugly around said extremity and to seal the inside of said tubular sleeve under the influence of said negative pressure.

7. The system of claim 6 wherein said lower seal comprises a rigid cap.

8. The system of claim 7 wherein a length of said tubular sleeve substantially equals a length of said extremity.

9. The system of claim 6 wherein said lower seal is a flexible flange adapted to fit snugly around said extremity and to seal the inside of said tubular sleeve under the influence of said negative pressure.

10. The system of claim 1 wherein said enclosing means comprises a pliant material for accommodating movements of said body portion.

11. The system of claim 1 wherein said vacuum system comprises:

a) a vacuum pump; and b) a connecting line between said vacuum pump and said enclosing means for evacuating said enclosing means down to said predetermined negative pressure, said predetermined negative pressure ranging between −20 mm Hg and −85 mm Hg relative to atmospheric pressure.

12. The system of claim 1 wherein said heating means is positioned outside said enclosing means, said thermal energy is a radiant energy form, and said enclosing means comprises a material transmissive to said radiant energy form.

13. The system of claim 12 wherein said heating means comprises a heat lamp.

14. The system of claim 1 wherein said negative pressure has a value between 0 mm Hg and −85 mm Hg relative to atmospheric pressure.

15. The system of claim 1 wherein said vacuum system comprises oscillating means for oscillating said negative pressure, thereby promoting a transport of said thermal energy to a core body of said mammal by a circulatory system of said mammal.

16. A method for core body warming of a mammal experiencing hypothermia, said method comprising the steps of:

a) enclosing a body portion of said mammal in a vacuum-tight manner, thereby defining an enclosure;

b) generating and maintaining a negative pressure within said enclosure, thereby causing a local vasodilation in said body portion; and c) delivering a thermal energy to a surface of said body portion while maintaining said negative pressure, so that said local vasodilation promotes absorption and transfer of said thermal energy from said surface to a core body of said mammal.

17. The method of claim 16 comprising the step of delivering said thermal energy from outside of said enclosure.

18. The method of claim 16 comprising the step of delivering said thermal energy from inside said enclosure.

19. The method of claim 16 wherein said negative pressure has a value between 0 mm Hg and −85 mm Hg relative to atmospheric pressure.

20. The method of claim 16 comprising the step of oscillating said negative pressure, thereby promoting a transport of said thermal energy to a core body of said mammal by a circulatory system of said mammal.

* * * * *